United States Patent [19]

Williams et al.

[11] 4,117,881
[45] Oct. 3, 1978

[54] SYSTEM FOR AND METHOD OF FREEZING BIOLOGICAL TISSUE

[75] Inventors: Thomas E. Williams, Millersville; Thomas A. Cygnarowicz, New Carrollton, both of Md.

[73] Assignee: The United States of America as represented by the Administrator of the National Aeronautics and Space Administration, Washington, D.C.

[21] Appl. No.: 806,440

[22] Filed: Jun. 14, 1977

[51] Int. Cl.[2] .......................................... F25B 13/00
[52] U.S. Cl. ........................................ 165/2; 165/30; 62/78; 62/514 R; 236/78 B; 128/1 R; 195/1.8; 219/299; 219/302
[58] Field of Search ................ 165/2, 30; 236/78 B; 128/1 R; 62/78, 514 R; 195/1.8; 219/30 R, 328, 299

[56] References Cited

U.S. PATENT DOCUMENTS

| 3,080,725 | 3/1963 | Cowley et al. | 62/62 |
|---|---|---|---|
| 3,389,744 | 6/1968 | Sullivan et al. | 165/30 |
| 3,485,245 | 12/1969 | Lahr et al. | 219/301 |
| 3,590,215 | 6/1971 | Anderson et al. | 219/299 |
| 3,648,475 | 3/1972 | Kiselev et al. | 62/514 |
| 3,805,883 | 4/1974 | Baldwin | 165/30 |
| 3,815,669 | 6/1974 | Lindenschmidt | 165/30 |
| 3,898,023 | 8/1975 | Faust | 62/62 |
| 3,952,536 | 4/1976 | Faust et al. | 128/1 R |
| 4,030,314 | 6/1977 | Strehler et al. | 62/78 X |

Primary Examiner—Charles J. Myhre
Assistant Examiner—Margaret A. LaTulip
Attorney, Agent, or Firm—Robert D. Marchant; John R. Manning; John O. Tresansky

[57] ABSTRACT

Blood cells, blood marrow, and other similar biological tissue is frozen while in a polyethylene bag placed in abutting relationship against opposed walls of a pair of heaters. The bag and tissue are cooled with refrigerating gas at a time programmed rate at least equal to the maximum cooling rate needed at any time during the freezing process. The temperature of the bag, and hence of the tissue, is compared with a time programmed desired value for the tissue temperature to derive an error indication. The heater is activated in response to the error indication so that the temperature of the tissue follows the desired value for the time programmed tissue temperature. The tissue is heated to compensate for excessive cooling of the tissue as a result of the cooling by the refrigerating gas. In response to the error signal, the heater is deactivated while the latent heat of fusion is being removed from the tissue while the tissue is changing phase from liquid to solid.

15 Claims, 2 Drawing Figures

SYSTEM FOR AND METHOD OF FREEZING BIOLOGICAL TISSUE

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

The present invention relates to a method of and apparatus for freezing blood cells, bone marrow and other similar biological tissue, and more particularly to such a system and method wherein the tissue is heated to compensate for excessive cooling of the tissue by a refrigerating gas.

There is a medical need for the preservation of blood cells, bone marrow, and other biological tissue. Long-term storage in the frozen state has proven to be a successful method and has been practiced for some years. It has been known for some time that the viability (survivability) of frozen blood cells and biological tissue depends upon the rate at which such material is frozen, i.e., the rate at which the tissue is transferred from the liquid to the solid state. Cell destruction can occur if freezing takes place excessively fast or slow. While the addition of cryoprotective agents helps alleviate the situation and has proven successful for certain cell types, freezing rate is still considered to be a primary factor in cell viability.

The purpose of the invention is to provide a more precise apparatus for and method of controlling the freezing rate of biological tissue and thereby permit medical researchers to establish the optimum (maximum viability) freezing rate, thus increasing the yield of frozen cells and, consequently, reducing the cost thereof.

It is another object of the invention to enable the yield of frozen white blood cells, bone marrow and other similar biological tissue to be increased to the point where they would find wide acceptance in the treatment and cure of disease.

In the prior art, before the freezing process begins, the tissue to be frozen is mixed with a cryoprotective agent in a container, e.g., an ampule or sample bag. Typically, the container is then placed in a standard, commercially available biological freezer. The freezer uses a liquid nitrogen freezing solution which vaporizes to provide cooling gas to which heat is transferred from the tissue being frozen. The system is programmed to drop the cooling gas temperature at a desired rate; i.e., control is maintained over the cooling gas and not the freezing sample (although the temperature of the outside surface of the sample is monitored and recorded). After the sample is completely frozen, it is quickly transferred to a storage freezer where it is kept until needed.

The prior art systems invariably encountered problems in maintaining temperature control of the freezing solution while the latent heat of fusion was being released from the freezing solution. At the freezing point of the tissue, a large amount of heat (compared to the cooling of the liquid or solid) must be removed to accomplish the change of state from liquid to solid. In an ideal solution, this change of state occurs at a constant fluid-solid temperature for the cells.

A disadvantage of the prior art system is that temperature control is maintained of the cooling gas rather than of the sample being frozen. Variations in thermal properties and quantity being frozen from one sample to another cause widely varying sample freezing rates, which is unsatisfactory because cell viability is strongly dependent on freezing rate.

It is, therefore, a further object of the invention to provide a new and improved apparatus for and method of freezing biological tissue consistently, regardless of variations in the properties and the quantity of the tissue.

Modifications of the above described system provide some improvement. For example, the temperature of the tissue can control the flow of liquid nitrogen refrigerant to the freezing chamber. However, freezer gas temperature response is slow and it has been found that a uniform, repeatable freezing curve for the tissue cannot be maintained.

Another modification to the previous freezing system involves increasing the flow of liquid nitrogen refrigerant to the freezing chamber when the sample being frozen reaches the freezing point. In reality, the freezing liquid experiences a subcooling effect near the freezing point. The temperature of the sample drops below the freezing temperature until freezing starts and rises a few degrees when freezing is initiated. By observing the output of a thermocouple located on the sample, one can tell when freezing starts. At this point, the liquid nitrogen refrigerant can be turned on at full flow to provide maximum cooling. Once again, however, the response of the cooling gas temperature is not fast enough to maintain the required cooling.

Attempts at programming the freezer to provide more or less cooling at different phases of the freezing process are unsuccessful because: (1) the occurrence time of the phase change from liquid to solid can vary from sample to sample, and (2) the freezer cooling gas cannot change temperature quickly enough.

SUMMARY OF THE INVENTION

In accordance with the present invention, blood cells, bone marrow, and other similar biological tissue are placed in a container having high thermoconductivity so that the tissue and container are at substantially the same temperature; preferably such a container is a polyethylene bag having a wall thickness on the order of 0.05 mm. Opposed surfaces of the bag abut against opposed walls of a pair of heaters. The container is cooled with refrigerating fluid at a timed programmed rate at least equal to the maximum cooling rate needed at any time during the freezing process for the tissue. The temperature of a surface of the container is monitored to derive an indication of the tissue temperature. The indication of the tissue temperature is compared with a time programmed, desired value for the tissue temperature to derive an error indication. The heater is activated in response to the error indication so that the temperature of the tissue follows the desired value for the time programmed tissue temperature. The tissue is heated to compensate for excessive cooling of the tissue as a result of the cooling by the refrigerating fluid. As the latent heat of fusion is being removed from the tissue while the tissue is changing phase from liquid to solid, the heaters are deactivated.

The heater is energized by electronic circuitry having a very high temperature resolution, e.g., 1/60° C, with a full power bandwidth of ½° C. The circuit is capable of going from zero to full energization of the heater in ½ second, so that a very fast response for activating the heater is attained, as is needed to prevent heating of the tissue while the latent heat of fusion is being removed, at the critical fusion temperature.

The circuitry for controlling the heater includes a thermocouple that abuts against the container and extends through an aperture in one of the heaters. The heater includes a pair of high thermoconductivity plates that, together with the bag, form a sandwich, enabling the thermocouple temperature to be substantially equal to the temperature of the tissue. The thermocouple signal is combined with a set point signal derived from a blood temperature program to derive an error signal that is compared with a relatively low frequency ramp. The relative amplitudes of the error signal and the ramp control the number of times that an electronic switch, such as a Triac, is activated during each cycle of the ramp generator. To attain the stated resolution and control, the number of pulses during each ½ second cycle of the ramp can vary anywhere from 0 to 60, in two-step increments.

It is, accordingly, a further object of the invention to provide a new and improved control circuit particularly adapted to energize a heater in response to a temperature indication, whereby the heater can be controlled to a very close thermal tolerance, over a relatively wide thermal bandwidth, with a fast response time.

These and other objects and advantages of this invention will become apparent upon reading the following description of which the attached drawings form a part.

DESCRIPTION OF THE PREFERRED EMBODIMENT

Figure 1:
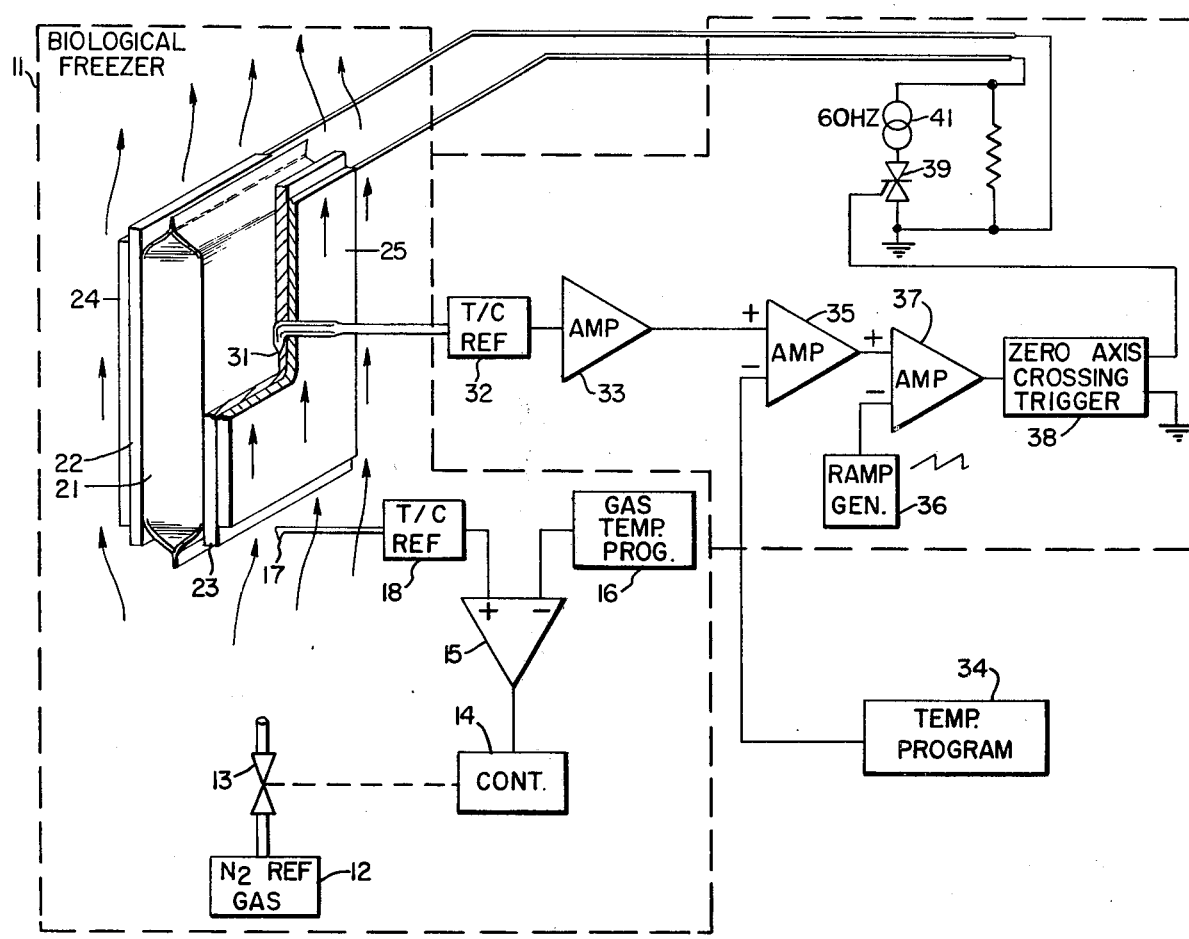
FIG. 1 of the drawing is a partially schematic and partially perspective drawing of a preferred embodiment of the invention.

Reference is now made to FIG. 1 of the drawing wherein there is schematically illustrated a biological freezer 11 of a conventional type, such as is available from the Linde Co. Freezer 11 includes a fluid refrigerant source 12, preferably a source of nitrogen gas. Refrigerant from source 12 is supplied to a volume being cooled by valve 13 that is controlled in response to a mechanical output of controller 14. Controller 14 is responsive to an error signal from differential amplifier 15 which in turn is responsive to a temperature indicating signal and a signal indicative of a desired temperature versus time relationship for the volume of freezer 11, as derived from gas temperature program source 16. The temperature indicating input signal to differential amplifier 15 is derived from a thermocouple 17 in the gaseous refrigerant flow stream, which thermocouple supplies an input signal to a conventional thermocouple reference circuit 18. Thermocouple reference circuit 18 derives output signals that are directly proportional to the temperature of the gas in the volume where the material being frozen is located.

Typically, in the prior art, blood cells, bone marrow and other similar biological tissue were frozen, i.e., changed from the liquid to the solid state, by placing the tissue in a polyvinyl container that was placed in the cooled volume of biological freezer 11. Typically, in the prior art, the output of gas temperature program source 16 had a linearly decreasing temperature versus time characteristic. Differential amplifier 15 responded to the outputs of reference circuit 18 and source 16 to derive a control signal that caused the temperature of the refrigerating gas to follow the programmed value derived from source 16.

It has been found that the temperature of the tissue being frozen follows the gas temperature only until the fusion temperature of the tissue is reached. When fusion begins, typically at −16° C, there is a step increase in the temperature of the tissue to −13° C. It takes approximately 4 additional minutes to overcome the rise in temperature at the fusion point of the tissue. Approximately 10 additional minutes are required before the temperature of the tissue is substantially the same as the temperature of the gaseous refrigerant.

In accordance with the present invention, these prior art problems are alleviated by deriving a signal that is substantially equal to the temperature of the tissue being frozen and controlling the application of heat to the tissue in response to the monitored temperature of the tissue. Also, the tissue is cooled with gas from source 12 at a rate at least equal to the maximum cooling rate needed at any time during the freezing process, a result that is attained by modifying the program of source 16. The tissue is heated to compensate for excessive cooling of the tissue as a result of the cooling by the refrigerating fluid. By virtue of a high resolution, fast response time feedback loop between the temperature measuring device and the heater, the heater is deactivated while the latent heat of fusion is being removed from the tissue while it is undergoing a change of state from liquid to solid.

To these ends, the tissue is placed in a polyethylene bag 21 having parallel faces that abut against opposed parallel walls of metal plates 22 and 23. On the outer walls of plates 22 and 23 are bonded electric heaters 24 and 25; to provide a better bond between the walls of the plates and the heaters, the walls are chemically etched. Heater plates 22 and 23 are arranged so that the gap between them extends in the vertical direction and bag 21 has its longitudinal axis similarly disposed. Because bag 21 is mounted vertically, in line with refrigerant gas flow to achieve maximum cooling of the tissue in bag 21, there is a moderate hydrostatic pressure of the liquid tissue in bag 21 that tends to push the heater plates apart. However, the plates 22 and 23 are sufficiently stiff, e.g., 0.75 mm thick of hardened aluminum, so that negligible bending and a uniform thickness of the tissue results, with uniform cooling of the tissue. Hardened aluminum is also preferably employed for plates 22 and 23 because of its high thermal conductivity to provide a good heat transfer between heaters 24 and 25 and the aluminum plates and the tissue in polyethylene bag 21. During the freezing process, the entire heater assembly, including plates 22 and 23 and heaters 24 and 25 is held together at the edge of the plates by a fiberglass channel (not shown).

In one configuration, the relatively high thermal conductivity of bag 21 is achieved by fabricating the bag of polyethylene with a wall thickness of 0.05 mm. The thickness of the bag, between its parallel faces that abut against plates 22 and 23 is relatively small, such as 4 mm, while the planar faces of the bag can be any suitable size. Bag 21 can be of a type commercially available from Union Carbide, and is provided with a self-sealing port so that cells can be injected and withdrawn from the bag under sterile conditions. In development work that was actually performed, bags having planar faces with areas of 13 cm by 18 cm were designed to hold up to 100 ml of blood cells; other bags having areas of 6 cm by 18 cm and 30 cm by 30 cm were also tested. Because of the construction of the heaters, and the thermal properties of the tissue in bag 21, as well as the thermal conductance properties of the bag, the temperature of the tissue within the bag is substantially equal to the temperature of the surface of the bag.

In one preferred configuration, each of heaters 24 and 25 includes a copper alloy foil sandwiched between two layers of Kapton film, achieving a total heater thickness of less than 0.2 mm. Such a heater design minimizes the thermal resistance path from the heaters to bag 21 and the cells within the bag and provides a fast response time because of the small thermal heat capacity of the heaters. The maximum power requirement for heaters 24 and 25 depends on the flow rate of liquid nitrogen past bag 21 and the maximum desired cooling rate of the tissue. It was experimentally determined that 280 watts is the maximum power required for the described configuration.

The described configuration of plates 22 and 23, as well as heaters 24 and 25, is advantageous because: (1) the thin section of tissue in the 4 mm gap between plates 22 and 23 minimizes thermal gradients within the tissue in container 21; (2) a standard blood retainer bag configuration can be employed; (3) it is easier to analyze and adapt the system for one-dimensional heat flow through bag 21; (4) it is easier to install the heater in the refrigerator; and (5) there is a compatibility with readily available, commercial gaseous biological freezers.

To monitor the surface temperature of bag 21 and thereby provide a signal substantially indicative of the temperature of the tissue within the bag, thermocouple 31 is centrally located against one face of the bag. To this end, a hole is drilled through plate 23 and heater 25 to enable the thermocouple to extend through the heater assembly into contact with the center of the face of bag 21. The temperature indicating output signal of thermocouple 31 is supplied to a negative feedback loop for controlling the amount of electric power applied to heaters 24 and 25, and therefore the temperature of bag 21 and the tissue therein.

The negative feedback loop includes a thermocouple reference circuit 32, of a known type, responsive to the signal derived by the thermocouple. The output signal of reference circuit 32 is a DC voltage directly proportional to the temperature monitored by thermocouple 31. The output signal of circuit 32 is applied to the input of DC, operational amplifier 33 which derives an output signal that is compared with a time varying signal derived from source 34, which signal is indicative of the desired or set point time vs. temperature trajectory for the tissue in container 21. The comparison between the signals derived from amplifier 33 and source 34 is performed by differential amplifier 35, which derives an error output signal having a magnitude directly proportional to the difference between the inputs thereof.

The magnitude of the error signal derived from amplifier 35 is converted into a rectangular wave having a duty cycle directly proportional to the error signal magnitude. To this end, the output of amplifier 35 is compared with the output of ramp generator 36 in differential amplifier 37. Ramp generator 36 derives a periodic, saw-tooth wave having a relatively long period, such as 0.5 seconds. The ramp output of generator 36 has a linear amplitude versus time characteristic over the 0.5 second interval and virtually zero flyback time. Comparator 37 responds to the ramp generator output and the error signal derived from amplifier 35 to derive a signal indicative of the difference between the error signal and ramp. The output of amplifier 37 is applied to a zero axis crossing trigger circuit 38 which derives positive voltage pulses at each positive transition of the load current in response to the difference signal from amplifier 37 being greater than zero; in response to the output of amplifier 37 being equal to or less than zero, a zero voltage level is derived from trigger circuit 38. Thereby, the number of pulses from the output of trigger circuit 38 is directly proportional to the deviation of the temperature monitored by thermocouple 31 from the desired blood temperature, over one cycle of ramp generator 36.

The output signal of trigger generator 38 controls an electric switch, in the form of Triac 39, that selectively connects heaters 24 and 25 to 60 Hz AC power source 41. Of course, the 60 Hz source cuts off Triac 39 twice during each cycle of the power source that the Triac has been activated into the conducting state in response to the positive voltage pulses derived from trigger circuit 38. Because power source 41 has a period much less than the 2 Hz output of trigger generator 38, many cycles of the power source occur during each cycle of the output of the trigger circuit. In the specifically described configuration, there is an opportunity to cut off Triac 39 60 times during each cycle of ramp generator 36 to provide a resolution of 1/60° C and a full power bandwidth of ½° C. The circuit is capable of going from zero to full power and vice versa in the ½ second period of ramp generator 36. Thereby, the heat applied by heaters 24 and 25, and plates 22 and 23, can be cut off or cut on at a very rapid rate. Because of the linear relationship between the variable duty cycle output of trigger circuit 38 and the error signal derived from amplifier 35, the amount of power supplied to the heater is proportional to the error signal.

Figure 2:
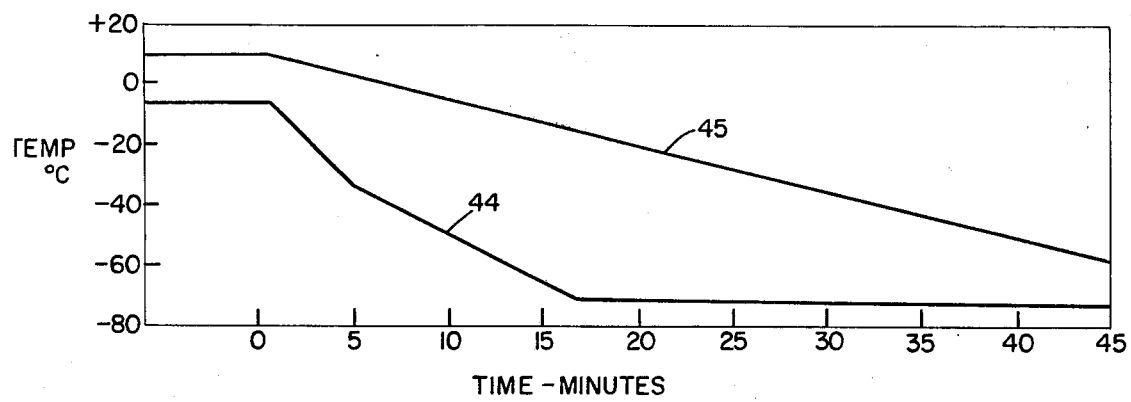
FIG. 2 includes two graphs indicating the programmed time variations of the temperatures of blood being frozen and refrigerant gas supplied to the blood.

Typical curves for the output signals at gas temperature program source 16 and blood temperature program source 34 are illustrated by waveforms 44 and 45, respectively, in FIG. 2. It has been found that the refrigerant gas and bag surface temperatures actually follow the desired curves indicated in FIG. 2. It is noted from curve 44 that the temperature of the gas supplied to the volume being cooled causes the tissue in container 21 to be cooled at a rate at least equal to the maximum cooling rate needed at any time during the freezing process. For example, initially the temperature of the gas is at approximately −5° C, in contrast to an initial temperature of the prior art method of approximately +20° C. Heat is supplied by heaters 24 and 25 and plates 22 and 23 to compensate for the excessive cooling of the tissue as a result of the cooling by the refrigerating gas. When the latent heat is being removed from the tissue in container 21, at the time the liquid is being fused to a solid, the heater is deactivated because of the tendency for the tissue to increase in temperature at this time, as indicated by the output of thermocouple 31. Hence, the step function increase which occurred in the prior art at the time fusion was occurring, no longer is observed.

Where there has been described and illustrated one specific embodiment of the invention, it will be clear that variations in the details of the embodiment specifically illustrated and described may be made without departing from the true spirit and scope of the invention as defined in the appended claims.

What is claimed is:

1. A method of freezing blood cells, bone marrow, and other similar biological tissue located in a container against opposed walls of a pair of heaters, said container having a high thermal conductivity so that the tissue and container are at substantially the same temperature, comprising cooling the container with refrigerating fluid at a time programmed rate at least equal to the maximum cooling rate needed at any time during the freezing process, monitoring the temperature of a surface of the container to derive an indication of the tissue temperature, comparing the indication of the tissue temperature with a time programmed desired value for the tissue temperature to derive an error indication, and activating the heaters in response to the error indication so that the temperature of the tissue follows the desired value for the time programmed tissue temperature.

2. The method of claim 1 wherein the container is a polyethylene bag.

3. The method of claim 1 wherein the bag has a relatively narrow width in a direction at right angles to its longitudinal axis, and flowing the fluid in the direction of said axis.

4. A method of freezing blood cells, bone marrow and other similar biological tissue comprising cooling the tissue with refrigerating fluid supplied to the tissue at a time programmed rate at least equal to the maximum cooling rate needed at any time during the freezing process, heating the tissue to compensate for excessive cooling of the tissue as a result of the cooling by the refrigerating fluid, and preventing heating of the tissue while the latent heat of fusion is being removed from the tissue while it is undergoing a change of state from liquid to solid.

5. A method of freezing blood cells, bone marrow and other similar biological tissue, comprising cooling the tissue with refrigerating fluid at a time programmed rate at least equal to the maximum cooling rate needed at any time during the freezing process, deriving an indication of tissue temperature, comparing the indication of the tissue temperature with a time programmed desired value for the tissue temperature to derive an error indication, and heating the tissue in response to the error indication so that the temperature of the tissue follows the desired value for the time programmed tissue temperature.

6. Apparatus for freezing blood cells, bone marrow and other similar biological tissue adapted to be placed in a container having a high thermal conductivity so that the tissue and container are at substantially the same temperature, comprising a heater having a pair of opposed heating walls against which the container is adapted to abut, means for cooling the container with refrigerating fluid at a time programmed rate at least equal to the maximum cooling rate needed at any time during the freezing process, means for monitoring the temperature of a surface of the container to derive an indication of tissue temperature, means for comparing the indication of the tissue temperature with a time programmed desired value for the tissue temperature to derive an error indication, and means for activating the heater in response to the error indication so that the temperature of the tissue follows the desired value for the time programmed tissue temperature.

7. The apparatus of claim 6 wherein the heater includes a pair of metal plates forming the opposed heating walls, an electric heater responsive to the activating means on each of said plates remote from each heating wall, said walls being flat and parallel to each other and having a gap between them so that flat, parallel faces of the container abut against them.

8. The apparatus of claim 7 wherein the plates are located in the path of the fluid so that the fluid flows at right angles to the width of the gap.

9. The apparatus of claim 7 further including a controller for the heater responsive to the temperature monitoring means, said controller including means for comparing a first signal indicative of the monitored temperature with a desired tissue temperature to derive a control signal having a duty cycle directly proportional to the deviation between the load and the desired temperature, an electric switch for selectively connecting the heater to an AC power source that is connected to the switch to cut off the switch during each cycle of the power source, the power source having a period much less than each period of the control signal so that many cycles of the power source occur during one cycle of the control signal, said switch being responsive to the control signal so that the switch is activated to connect the power source to the heater during a portion of each cycle of the control signal while the duty cycle of the control signal is being derived, whereby the heater is cut off and activated with a response time determined by the frequency of the power source to heat the tissue to compensate for excessive cooling of the tissue by the refrigerating fluid and to prevent heating of the tissue while the latent heat of fusion is being removed from the tissue while it is undergoing a change of state from liquid to solid.

10. The apparatus of claim 9 wherein the means for deriving the control signal includes means for comparing the first signal wiith the desired tissue temperature to derive an error signal having an amplitude directly indicative of the deviation, a periodic linear waveform source having a relatively long period, means for comparing the amplitudes of error signal and the waveform to derive a control signal having a duty cycle over each period of the waveform directly proportional to the magnitude of the deviation.

11. Apparatus for freezing blood cells, bone marrow and other similar biological tissue comprising means for cooling the tissue with refrigerating fluid at a time programmed rate at least equal to the maximum cooling rate needed at any time during the freezing process, means for deriving an indication of tissue temperature, means for comparing the indication of the tissue temperature with a time programmed desired value for the tissue temperature to derive an error indication, and means for heating the tissue in response to the error indication so that the temperature of the tissue follows the desired value for the time programmed tissue temperature.

12. The apparatus of claim 11 wherein the heater includes a pair of metal plates forming the opposed heating walls, an electric heater responsive to the error indication on each of said plates remote from each heating wall, said walls being flat and parallel to each other and having a gap between them so that flat, parallel faces of a container for the tissue abut against them.

13. The apparatus of claim 12 wherein the plates are located in the path of the fluid so that the fluid flows at right angles to the width of the gap.

14. Apparatus for controlling the temperature of a load to a high resolution, said load being located in a refrigerator adapted to freeze the load, comprising means for sensing the temperature of the load to derive a first signal indicative of the load temperature, means for comparing the first signal with a desired load temperature to derive a control signal having a duty cycle directly proportional to the deviation between the load and desired temperatures, an electric heater for heating the load, an electric switch for selectively connecting the heater to an AC power source that is connected to the switch to cut off the switch during each cycle of the power source, the power source having a period much less than each period of the control signal so that many cycles of the power source occur during one cycle of the control signal, said switch being responsive to the control signal so that the switch is activated to connect the power source to the heater during a portion of each cycle of the control signal while the duty cycle of the control signal is being derived.

15. The apparatus of claim 14 wherein the means for deriving the control signal includes means for comparing the first signal with the desired load temperature to derive an error signal having an amplitude directly indicative of the deviation, a periodic linear waveform source having a long period relative to the period of the AC power source, means for comparing the amplitudes of the error signal and the waveform to derive a control signal having a duty cycle over each period of the waveform directly proportional to the magnitude of the deviation.

* * * * *